United States Patent
Simon et al.

(10) Patent No.: US 11,813,339 B2
(45) Date of Patent: *Nov. 14, 2023

(54) METHOD OF USE FOR THERAPEUTIC BONE AGENTS

(71) Applicant: IGL Pharma, Inc., Angleton, TX (US)

(72) Inventors: Jaime Simon, Angleton, TX (US); R. Keith Frank, Lake Jackson, TX (US)

(73) Assignee: IGL PHARMA, INC., Angleton, TX (US)

( * ) Notice: Subject to any disclaimer, the term of this patent is extended or adjusted under 35 U.S.C. 154(b) by 187 days.

This patent is subject to a terminal disclaimer.

(21) Appl. No.: 16/484,706

(22) PCT Filed: Feb. 6, 2018

(86) PCT No.: PCT/US2018/017082
§ 371 (c)(1),
(2) Date: Aug. 8, 2019

(87) PCT Pub. No.: WO2018/148209
PCT Pub. Date: Aug. 16, 2018

(65) Prior Publication Data
US 2021/0138095 A1    May 13, 2021

Related U.S. Application Data

(60) Provisional application No. 62/456,191, filed on Feb. 8, 2017.

(51) Int. Cl.
| | |
|---|---|
| *A61K 51/00* | (2006.01) |
| *A61M 36/14* | (2006.01) |
| *A61K 51/04* | (2006.01) |
| *A61P 35/00* | (2006.01) |
| *A61P 35/04* | (2006.01) |
| *A61P 19/08* | (2006.01) |
| *A61P 7/00* | (2006.01) |
| *G21G 1/02* | (2006.01) |

(52) U.S. Cl.
CPC ...... *A61K 51/0482* (2013.01); *A61K 51/0478* (2013.01); *A61P 35/00* (2018.01); *A61P 7/00* (2018.01); *A61P 19/08* (2018.01); *A61P 35/04* (2018.01); *G21G 1/02* (2013.01)

(58) Field of Classification Search
CPC . A61K 51/0482; A61K 51/0478; A61P 35/00; A61P 7/00; A61P 19/08; A61P 29/02; A61P 35/04; G21G 1/02
See application file for complete search history.

(56) References Cited

U.S. PATENT DOCUMENTS

| 5,059,412 A | 10/1991 | Simon et al. |
| 10,172,965 B2 * | 1/2019 | Simon .................. A61P 7/00 |
| 10,596,277 B2 * | 3/2020 | Simon .................. A61P 35/00 |
| 2016/0250359 A1 | 9/2016 | Simon et al. |
| 2016/0287720 A1 | 10/2016 | Liu et al. |

FOREIGN PATENT DOCUMENTS

| WO | 2015/054173 | 4/2015 |
| WO | 2016/191413 | 12/2016 |

OTHER PUBLICATIONS

Sartor (Rev. Urol. 2004, 6, S3-S12).*
Chakraborty et al. (Nucl. Med. Comm. 2004, 25, 1169-1176).*
H. Fischer et al., Radionuclidic purity aspects of 153Sm for radionuclide therapy, Proceedings of the International Congress of the International Radiation Protection Agency, May 2004.

* cited by examiner

*Primary Examiner* — Michael G. Hartley
*Assistant Examiner* — Melissa J Perreira
(74) *Attorney, Agent, or Firm* — Technology Law PLLC; Karen L Kimble

(57) ABSTRACT

This invention relates to radioactive, bone-seeking, pharmaceutical compositions that are administered multiple times to a patient, have a lower impurity profile, a longer shelf life, and are less expensive to prepare.

10 Claims, 3 Drawing Sheets

Long-lived impurities in High Specific Activity Sm-153

METHOD OF USE FOR THERAPEUTIC BONE AGENTS

BACKGROUND OF THE INVENTION

Field of the Invention

The invention relates a method of use of bone-seeking radioactive metal-chelant formulations that are suitable for administration to a patient having: bone pain; one or more calcific tumors; or in need of a bone marrow suppression procedure, where that method of treating a patient involves multiple treatments with low specific activity (LSA) Sm-153 1,4,7,10-tetraazacyclododecanetetramethylenephosphonic acid (DOTMP).

Description of Related Art

Bone cancer can be primary or metastatic. Primary cancer occurs when the bone cells themselves are cancerous, and although this is a relatively rare disease, it is a very aggressive one, primarily effecting younger patients. Present treatment options include chemotherapy and external beam therapy, and in many patients an affected limb is amputated. Metastatic bone cancer occurs when cancer cells from soft tissue cancers grow on the bone. Cancers arising from prostate, breast and lung have a significant propensity to metastasize to bone in this way. Metastatic bone cancer can be associated with significant pain, decreasing the patient's ability to function. Controlling the pain is accomplished by increasing amounts of narcotics, significantly decreasing quality of life for the patient.

Radiopharmaceuticals, radioactive drugs, have been used as treatments for bone cancers. Cancer cells growing in the bone cause higher turnover of the bone in close proximity to them. The strategy for these drugs is to target this fast-growing bone. Note that these bone-seeking radiopharmaceuticals do not target cancer cells themselves but the nearby bone tissue.

Two classes of these radiopharmaceutical agents have been used for this purpose. The first class involves a radioactive metal salt. Examples of such agents are Sr-89 and Ra-223, both formulated as the chloride salt. These metals mimic calcium and thus concentrate in bone. Strontium-89 has a long half-life (50.57 days) and a high beta energy (maximum beta energy is 1.463 MeV). These two characteristics in conjunction with the lack of an imageable gamma photon have significantly reduced the use of this Sr-89 agent. Radium-223 is an alpha-emitting radioisotope that follows a decay chain producing a variety of daughter isotopes. The range of alpha particles is very short (about 0.1 mm) compared to that of beta particles (about 0.3 mm) and may limit the utility of Ra-223 to effectively treat bone cancer.

A second class of bone-seeking radiopharmaceuticals is comprised of phosphonic acid chelates, such as Sm-153-ethylenediaminetetramethylenephosphonic acid in which the radioactive Sm is chelated to the phosphonic acid, ethylenediaminetetramethylenephosphonic acid (EDTMP). One such example is Quadramet® (trademark of EUSA PHARMA (USA), INC) that is a commercially available chelate formed between Sm-153 and EDTMP that is currently indicated for the pain associated with bone metastases (U.S. Pat. No. 4,898,724).

U.S. Pat. No. 5,059,412 teaches the use of Sm-153, Gd-159, Ho-166, Lu-177 and Yb-175 chelates with chelants derived from the 1,4,7,10-tetraazacyclododecane moiety including 1,4,7,10-tetraazacyclododecanetetramethylenephosphonic acid (DOTMP), while U.S. Pat. No. 5,064,633 teaches the above metals plus Y-90.

A therapeutically effective biodistribution (fate of the activity after administration) for a therapeutic bone agent includes high bone uptake, low soft tissue uptake, rapid clearance of the activity not associated with bone, and high lesion-to-normal bone ratio. Compositions that do not have these characteristics are detrimental to the patient. For example, high soft tissue uptake would result in the patient receiving a high radiation dose to the liver, bone marrow or other soft tissue leading to undesirable side effects.

The phosphonic acid ligand keeps the Sm soluble and delivers it to bone. In this case the decay of Sm-153 gives off beta particles, which are useful for treating the tumor, and gamma photons which are useful for determining the fate of the isotope via gamma camera imaging. Also the half-life of Sm-153 is about 46 hours. Although these conditions seem ideal, the EDTMP/Sm complex is relatively labile and therefore there is a need to use a large excess of chelating agent relative to Sm (about 300:1 ligand to metal ratio). Because of this excess ratio, it is also necessary to use high specific activity (HSA) Sm-153. The preparation of HSA samarium-153 results in a significant amount of long-lived radionuclidic impurities (see FIG. 2). These long-lived isotopes make waste disposal more difficult and these isotopes accumulate in a patient's bone when they undergo multiple treatments. In a study by Sinzinger et al., QJ NUCL MED MOL IMAGING 2001; 55:420-30), they discuss the long-lived impurities such as Eu-154, present in Sm-153 EDTMP when multiple doses are administered to patients using high-resolution gamma spectroscopy as whole body counters (see FIG. 3). Their results showed that the undesirable doses due to the Eu isotopes increases with every treatment. The effect of the long-lived isotopes in patients is unknown, therefore this accumulation is undesirable.

All currently available radiopharmaceuticals for this purpose have drawbacks, and there is a need for an improved radiopharmaceutical agent to treat bone cancer.

Toward that purpose, the inventions discussed in WO 2015/054173 and WO 2016/191413 have been made by the present applicant and which are hereby incorporated by reference. WO 2015/054173 discloses a method for treating patients with LSA Sm-153 DOTMP and a 2 vial kit. WO 2016/191413 discloses an improved kit formulation having 3 vials that enables LSA Sm-153 DOTMP to be made more accurately and easily at a radiopharmacy.

Radionuclides such as Sm-153 are prepared in a nuclear reactor by bombarding purified targets of the element containing one less neutron and in the process generate radionuclidic impurities. For example, to produce Sm-153 the target that is irradiated is Sm-152 and Eu-154 is an unwanted impurity that is also formed.

The impurities can be detrimental to institutions from both a patient and a waste disposal standpoint. For example, too much Eu-154 administered to a patient would result in the isotope giving an undesirable dose to a patient for a long period of time, especially when multiple injections for treatment are done. In addition, the dose that is excreted in the urine by the patient containing Eu-154 is a concern and institutions may be forced to collect the radioactive urine. Disposal of the product vials containing residual activity can be a problem. These vials and syringes are typically allowed to decay for 10 half-lives prior to disposal. This is a reasonable amount of time for Sm-153 (about 20 days) but not for Eu-154 (about 86 years). Processes must be implemented in order to deal with waste disposal of vials and syringes that are used. This makes the use of these types of radiopharmaceuticals more complex and institutions may chose not to use the drugs.

In addition, these long-lived impurities cause issues with the radioactive licensing process for the facility. Typically institutions are only allowed small amounts of long-lived radionuclides (having half-lives greater than 120 days) before they are required to have financial assurance. Financial assurance can be very expensive, especially for institutions that only handle short-lived isotopes.

The specifications for Quadramet® (Sm-153 EDTMP) call for the product to contain less than 0.093 microcuries of Eu-154 per millicurie of Sm-153 at expiry (http://health-.phys.iit.edu/extended_archive/0001/msg00922.html, http://acnp-cal.org/SM153INS.html) or 4 days from the manufacture date (http://www.ibamolecular.eu/products/quadramet). This restriction limits the expiration time of the drug. Since Sm-153 decays faster than Eu-154, the longer the Sm-153 solution decays, the higher the amount of Eu-154 is in the sample relative to Sm-153. Thus expiration of not only formulated Quadramet® (e.g. Ca-EDTMP+Sm-153) but also the Sm-153 used to produce Quadramet® is limited by the amount of Eu-154 in the sample.

In nuclear reactors such as the one at the University of Missouri in Columbia MO, the Sm-152 samples are irradiated for one week in the "flux trap" (see FIG. 1) in order to produce the high specific activity (HSA) Sm-153 required for the production of Quadramet®. The flux trap is only accessed once a week and therefore high specific activity Sm-153 can only be produced on a weekly basis. Because of the growing amount of Eu-154 compared to Sm-153 over time, the Sm-153 isotope can only be used for a short period of time. Thus the drug is not available to treat patients on some days of the week. The flux trap portion of the reactor is also the most expensive to access (requiring reactor shut-down) thus increasing the production cost of the HSA Sm-153 isotope.

Clearly, there is a need for a product with a longer shelf life and a better impurity profile for use for multiple treatments to patients.

BRIEF SUMMARY OF THE INVENTION

The present invention provides a method for the treatment of a patient having bone pain, one or more calcific tumors, or in need of a bone marrow suppressing procedure, comprising administering to said patient multiple doses of a pharmaceutically-acceptable formulation of a chelate composition comprising a Clinically Relevant Dosage of the composition that is therapeutically effective in multiple injections without the accumulation of long-lived isotopes in the patient, wherein the Sm-153 used to prepare said composition possesses an extended Expiration Date of greater than or equal to about 5 days based on the Eu-154 present in the formulation being less than 0.093 µCi Eu-154 per mCi Sm-153. The chelate composition comprises LSA Sm-153 and DOTMP or a physiologically-acceptable salt thereof wherein the Sm-153 dosage is at least about 30 mCi per dose.

Each treatment results in lower toxicity to the bone marrow and a less accumulation of long-lived radionuclidic isotopes in the patient when compared with use of HSA Sm-153 chelates. The present invention involves the treatment of such bone cancer using low specific activity (LSA) Sm-153 chelated to a macrocyclic chelating agent, DOTMP. LSA Sm-153-DOTMP is easier and more readily available to prepare and incurs significantly lower cost in comparison to high specific activity (HSA) Sm-153. This was discussed in WO 2015/054173 which is hereby incorporated by reference. The present invention provides the use of this LSA Sm-153 DOTMP as a multiple injection treatment to the patient or patient without the undesired accumulation of long-lived isotopes such as Eu-154.

DETAILED DESCRIPTION OF THE INVENTION

Figure 1:
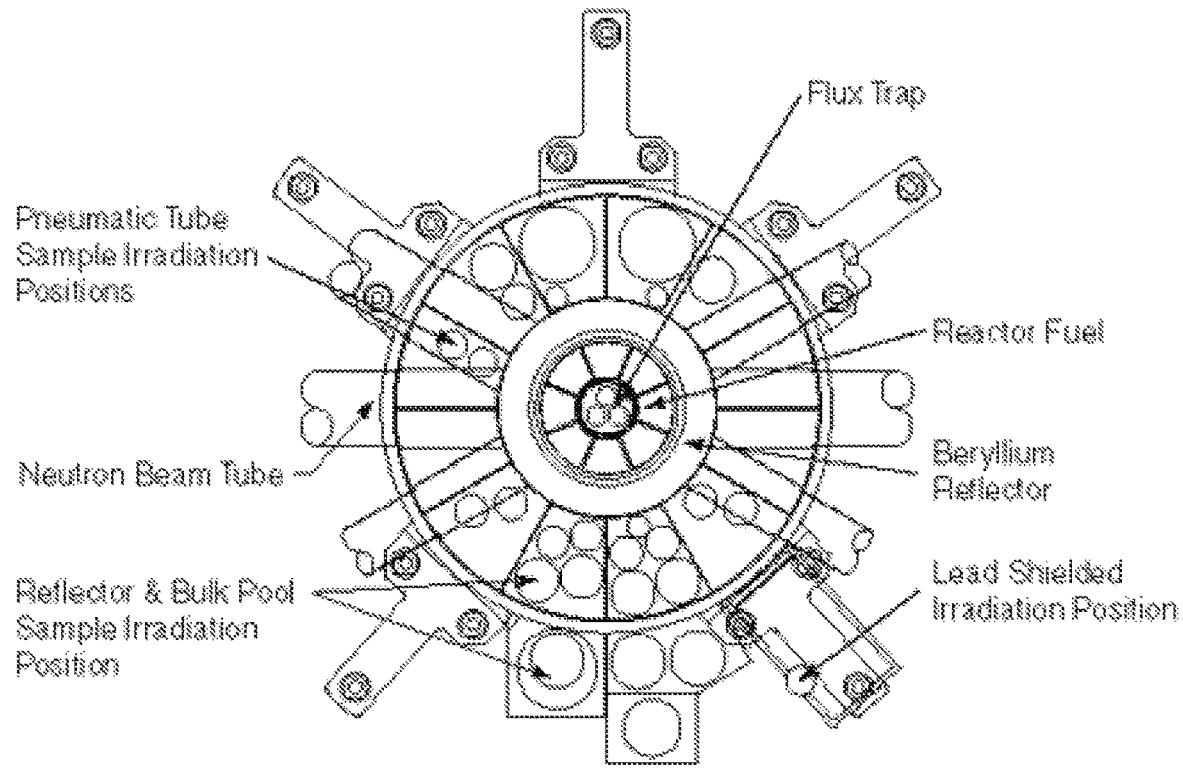
FIG. 1: Schematic of the available irradiation positions at the University of Missouri Research Reactor (MURR). High specific activity (HSA) Sm-153 is prepared in the flux trap which requires reactor shut down and is expensive. Low specific activity (LSA) Sm-153 is prepared in the reflector, which is much easier to access and can be done frequently. Provided courtesy of MURR.

It is understood that the terminology used herein is for the purpose of describing particular embodiments only and is not intended to be limiting. As used in this specification, the singular forms "a", "an", and "the" include plural referents unless the content clearly indicates otherwise. The following terms in the Glossary as used in this application are to be defined as stated below and for these terms, the singular includes the plural.

Various headings are present to aid the reader, but are not the exclusive location of all aspects of that referenced subject matter and are not to be construed as limiting the location of such discussion.

Also, certain US patents and PCT published applications have been incorporated by reference. However, the text of such patents is only incorporated by reference to the extent that no conflict exists between such text and other statements set forth herein. In the event of such conflict, then any such conflicting text in such incorporated by reference US patent or PCT application is specifically not so incorporated in this patent.

Glossary

% means weight percent, unless stated otherwise

Patient means any warm-blooded animal or mammal or human; any of which can be treated as described for this invention Clinically Relevant Dosage means enough activity to cause either pain palliation or reduction of tumor burden. This dosage is about 0.5 mCi per kg body weight or about 30 mCi per dose for a 70 kg patient; more preferred 1.0 mCi per kg body weight or about 70 mCi per dose for a 70 kg patient. Higher amounts of radioactivity may be administered to the patients or for treating tumor regression or bone marrow ablation in patients.

DOTMP means 1,4,7,10-tetraazacyclododecanetetramethylenephosphonic acid

EDTMP means ethylenediaminetetramethylenephosphonic acid Expiration Date means the number of days after production when Sm-153 contains equal to or greater than 0.093 µCi of Eu-154 per mCi of Sm-153.

FDA means US Food and Drug Administration

HSA means high specific activity that for Sm-153 is defined as greater than about 4 Ci/mg that is prepared by irradiating at a neutron flux greater than 1E14 neutrons/m$^2$ sec for greater than 120 hours LSA means low specific activity that for Sm-153 is defined as less than about 4 Ci/mg and is prepared by irradiating at a neutron flux less than about 1E14 neutrons/m$^2$ sec for less than 120 hours Ci means curies µCi means microcuries mCi means millicuries Multiple Doses means treatment of the patient with two or more doses of a Clinically Relevant Dosage of Sm-153 DOTMP, the number of doses can be from 2 to an indefinite number of doses, such as 5 to 100 doses to a patient; these doses are generally spaced over time such as at every 3 months, 6 months or 12 months intervals

DISCUSSION

The specific activity of an isotope is sometimes a source of confusion because it is expressed in many ways (see Practical Aspects of labeling DTPA and DOTA peptides with Y-90, In-111, Lu-177 and Ga-68 for Peptide-Receptor Scintigraphy and peptide-Receptor Radionuclide Therapy in preclinical and Clinical Applications at http://pharmacyce.unm.edu/program_information/freelessonfiles/Vol16Lesson5.pdf).

For this invention, the specific activity of an isotope is defined as the radioactivity (mCi or Bq) of the isotope in question divided by the mass of all of the isotopes (stable and radioactive) of the element. For example for reactor produced Sm-153 where the starting material is Sm-152 that is converted to Sm-153, the specific activity of Sm-153 is the amount of radioactivity of Sm-153 in the sample divided by the total mass of any Sm element in the sample (e.g. activity Sm-153/sum of masses of Sm-152 and Sm-153). The units of the number are typically in Curies per gram (Ci/g) or Curies per mole (Ci/mole). In some cases the percent of the isotope that is radioactive is reported. For example in reactor produced Sm-153, only about 2% of the Sm is Sm-153 and about 98% is non-radioactive Sm-152.

Traditionally, nuclear medicine scientists strive to increase the specific activity of the isotopes of interest. For example, two government grants for providing high specific activity isotopes have been recently awarded (*High Specific Activity Sm-153 by Post Irradiation Isotope Separation*, DOE SBIR grant Solicitation Number DE-FOA-0000676, and *Production of Commercial High Specific Activity Sn-117m Radiochemical and Chelates*, DOE grant Solicitation Number DE-FOA-000782). The use of high specific activity (HAS) isotopes allows for less mass of the isotope needed to achieve the same amount of radioactivity. This leads to lower amounts of chelating agents and/or proteins needed in the radioactive drug. In addition, in many cases such as with labeled antibodies and proteins, the receptors on cells (such as cancer cells) that the drugs target are limited. If the specific activity of the isotope is low (e.g. 2% of the atoms are radioactive), then the amount of active drug that reaches the target is relatively small. However, if the specific activity is high (a larger percentage of the atoms are radioactive), then the amount of effective drug that reaches the target is much higher, which explains why so much effort is put forth in radioisotope production to achieve higher and higher specific activity.

Contrary to this conventional wisdom where higher specific activity isotopes are sought-after as desirable, this invention utilizes Sm-153 produced in a lower flux portion of the nuclear reactor (reflector) for a shorter period of time (see FIG. 1), resulting in a lower specific activity (LSA) isotope with a significant cost reduction and lower impurity profile. When combined with DOTMP a product can be produced which comprises a Clinically Relevant Dosage of Sm-153-DOTMP with a reduced radionuclidic impurity profile, a longer shelf life, a lower cost to manufacture, and can be made available to patients on a more frequent basis. Since the toxicity due to accumulated long-lived isotopes in multiple dosing regimens (see FIG. 2) is unknown, it is prudent to reduce these long-lived isotopes in the formulation by utilizing LSA Sm-153. This in turn allows multiple doses of the LSA Sm-153 chelated to DOTMP to be administered. For example more than two doses to the patient up to 100 doses or more.

The present invention provides a method for the treatment of a patient having bone pain, one or more calcific tumors, or in need of a bone marrow suppressing procedure, comprising administering to said patient a pharmaceutically-acceptable formulation of a chelate composition comprising a Clinically Relevant Dosage of the composition that is therapeutically effective as Multiple Doses without a quantifiable accumulation of long-lived isotopes in the patient, said composition possessing an extended Expiration Date of the Sm-153 used to prepare the composition of greater than or equal to about 5 days based on Eu-154 present in the formulation being less than 0.093 µCi Eu-154/mCi Sm-153 and said chelate comprises LSA Sm-153 and DOTMP or a physiologically-acceptable salt thereof. The Clinically Relevant Dosage is about 0.3 to about 1.5 mCi/kg of body weight, preferred is about 0.5 mCi per kg body weight or about 30 mCi per dose for a 70 kg patient; more preferred 1.0 mCi per kg body weight or about 70 mCi per dose for a 70 kg patient. The Expiration Date, meaning the number of days after production when Sm-153 contains equal to or greater than 0.093 µCi of Eu-154 per mCi of Sm-153, is 5 days, 10 days or more at expiry. Multiple Doses are at least 5 doses for a patient that is administered at 3 month intervals; or 10 doses for a patient that is administered at 6 month intervals for the last 5 doses.

This invention provides a better radiopharmaceutical for the treatment of bone cancer for the following reasons. The radiopharmaceutical consists of LSA Sm-153 combined with the chelating agent, DOTMP. Unlike the chelate formed between Sm and EDTMP, a commercial product for comparison, the present Sm-DOTMP complex is not labile and does not easily dissociate. For that reason, it is possible to prepare a stable complex using a much smaller ratio of DOTMP to Sm-153 (about 1:1 ligand to metal ratio), compared to Sm-EDTMP (about 300:1 ligand to metal ratio). Additionally, this stability allows for the possibility of using LSA Sm-153 which is more readily available, less expensive, and has significantly fewer long-lived radionuclidic impurities compared to HSA Sm-153 (see FIG. 2). In addition, the bone marrow toxicity associated with a dose of Sm-153-DOTMP is less than that for an equivalent dose of Sm-153-EDTMP. While not wishing to be bound by theory, it is believed that the reason for this lessened toxicity is that the Sm-DOTMP chelate is more stable thereby allowing less free metal to be released in the formulation and that the chelate may also have less free metal available as it is diluted in the bloodstream of a patient. Small amounts of free metal can enter the bloodstream and precipitate as particles that can be taken up by bone marrow. Small amounts of radioactive Sm-153 directly deposited in the marrow in this way may be responsible for additional bone marrow toxicity. This stability is important when multiple doses are desired for treatment.

The formulations of the present invention may be in a kit form such that the two components (chelant and isotope) are mixed at the appropriate time prior to use or in a three component kit as described in WO 2016/191413. Whether pre-mixed as the drug or as a kit where the drug is made on site, the formulations require a pharmaceutically-acceptable carrier. Such carriers comprise any suitable pharmaceutically-acceptable carrier such as one or more of a suitable solvent, preservatives, diluents, excipients and buffers. Useful solvents include, for example, water, aqueous alcohols and glycols. The formulation is administered to the patient by injection intramuscularly or intravenously, or near the tumor or upstream of the blood supply to the tumor.

The present chelate composition comprises a Clinically Relevant Dosage of the composition that is therapeutically effective and pharmaceutically-acceptable, said composition possessing an extended Expiration Date of the Sm-153 used to prepare the composition that is greater than or equal to about 5 days and said chelate comprises Sm-153 and DOTMP or a physiologically-acceptable salt thereof. This composition is prepared from Sm-153 that at end of irradiation has a specific activity is less than 3 Ci/mg and a Eu-154 concentration less than 10 µCi Eu-154 per Ci Sm-153 at end of irradiation. This composition is prepared from Sm-153 that was produced in a nuclear reactor at a flux less than 1E14 neutrons/cm$^2$-sec and said chelate comprises Sm-153 and DOTMP or a physiologically-acceptable salt thereof wherein the Sm-153 dosage is at least 30 mCi.

The invention will be further clarified by a consideration of the following examples, which are intended to be purely exemplary of the invention.

Materials and Equipment:

The radioactive isotopes were purchased from The University of Missouri Research Reactor.

Chelants were purchased from commercial sources or were prepared as described in U.S. Pat. No. 5,059,412.

General Procedure

In the following examples, the lettered examples are comparative, and the numbered examples are this invention.

Example A: Comparative—Production of Sm-153 in MURR (University of Missouri Research Reactor) Reactor Flux Trap One mg of Sm-152, as Samarium oxide, was sealed in a quartz vial and irradiated for approximately 150 hours in the flux trap at MURR (HSA). The ratio of Eu-154 to Sm-153 at end of irradiation was approximately 18 µCi Eu-154 per Ci of Sm-153.

Example B: Comparative—Treatment of Patients with Flux Trap-Irradiated Sm-153 (HSA)

The Sm-153 prepared as in Example A was used to prepare doses of Sm-153-EDTMP. These doses were used to treat patients suffering from bone cancer. Patients were repeatedly treated (10 times) with 30 mCi of Sm-153-EDTMP as prepared in this example. The first 5 doses were given at 3 month intervals, and the second five doses given at 6 month intervals. After the decay of Sm-153, a NaI crystal was used to detect the amount of residual activity in the patients. After receiving 7 doses, there were significant amounts of activity detected in patients, which increased with each dose given thereafter. The activity was due to long-lived radionuclidic impurities created during the target irradiation process.

Example C: Comparative—Vienna Protocol by Dr. Helmut Sinzinger et al., QJ NCUL MED MOL IMAGING 2001; 55:420-30)

About 550 patients were repeatedly dosed with 30 mCi of Sm-153-EDTMP to treat prostate and breast bone metastases for pain palliation. These multiple does were as follows: 5 at 3 month intervals; 5 at 6 month intervals; 5 at 9 month intervals; and several indefinitely at 12 month intervals.

Figure 2:
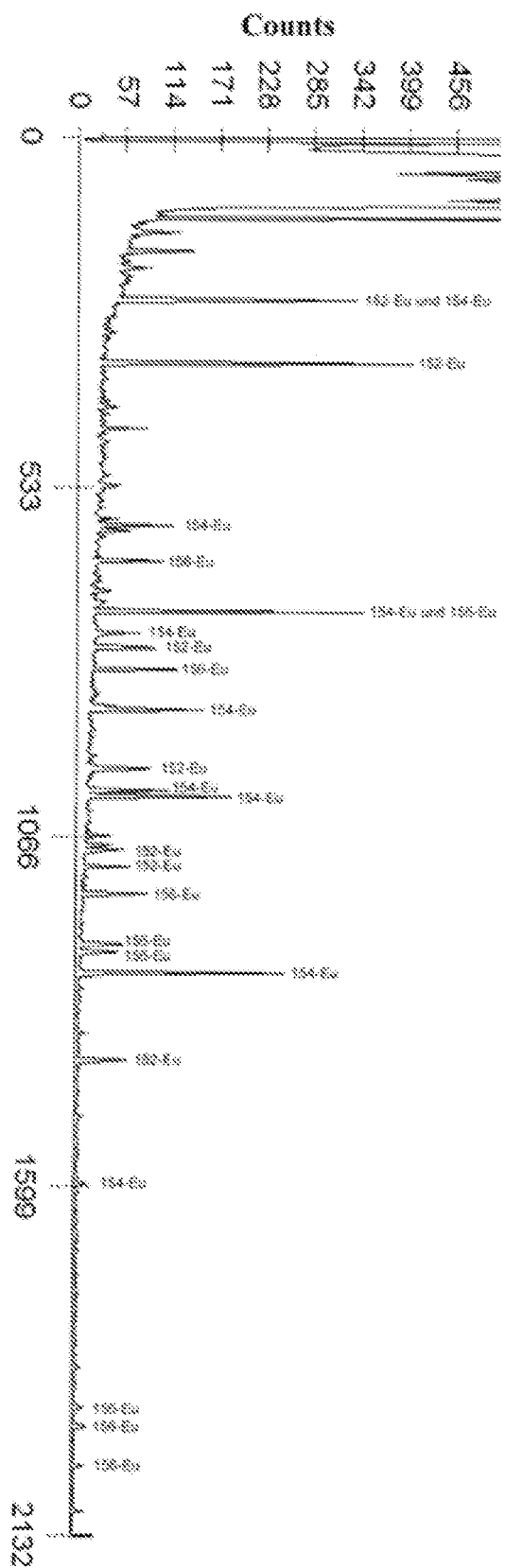
FIG. 2: High resolution gamma spectra of HSA Sm-153 showing long lived radioactive impurities. H. Fisher, et al., "Radionuclidic purity aspects of Sm-153 for radionuclide therapy," Proceedings of the International Congress of the International Radiation Protection Agency, May, 2004.
Figure 3:
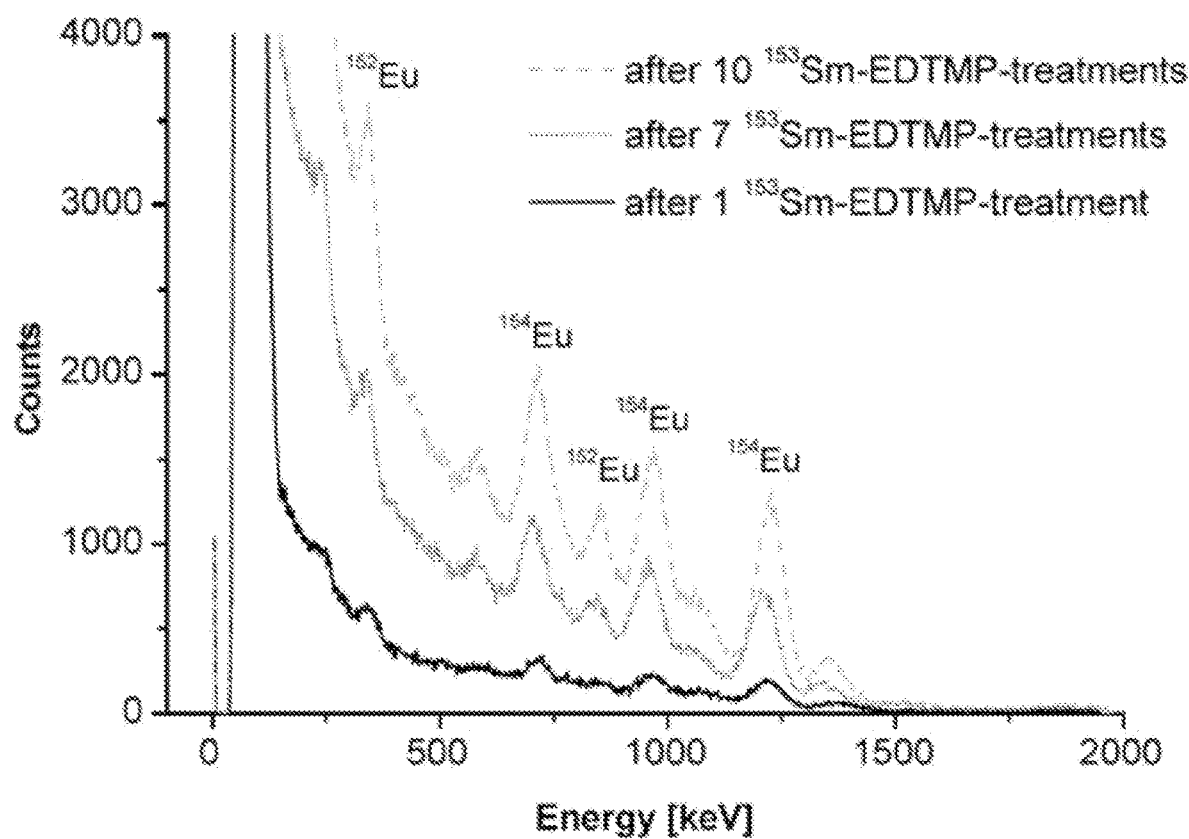
FIG. 3: Radioactive Eu-impurities detected in bone after 1, 7 and 10 treatments with 153Sm-EDTMP. H. Fisher, et al., "Radionuclidic purity aspects of Sm-153 for radionuclide therapy," Proceedings of the International Congress of the International Radiation Protection Agency, May, 2004.

The results showed lesion regression and improved survival. However, the long-lived impurities in HSA Sm-153-EDTMP were apparent as shown in FIG. 2. The build-up of these long-lived isotopes is seen in FIG. 3.

Example 1: Production of Sm-153 in MURR Reflector (LSA)

One mg of Sm-152, as Samarium oxide, was sealed in a quartz vial and irradiated for 2 days in the reactor reflector at MURR. The ratio of Eu-154 to Sm-153 at end of irradiation was approximately 0.5 µCi of Eu-154 per Ci of Sm-153.

Example 2: Treatment of Dogs with LSA Sm-153-DOTMP

Seven dogs with osteosarcoma were treated with the Sm-153-DOTMP made from LSA Sm-153 of Example 1 at 1 mCi/kg. There was uptake in the tumor for all dogs. The dogs displayed about one half of the myelosuppression of similar dogs treated with 1 mCi/kg of HSA Sm-153-EDTMP as evidenced from the nadir in platelets and neutrophils.

Example 3: MTD of LSA Sm-153-DOTMP

An ascending dose trial of 13 dogs starting at 1.5 mCi/mg was done which showed uptake in tumor for all seven dogs tested. The maximum tolerated dose is 1.75-2.0 mCi/kg; whereas for Sm-153-EDTMP the maximum tolerated dose was 1.0 mCi/kg. Stable or improved indices were experienced by 7 of 12 dogs.

Example 4: Treatment of Patients with Reflector-Irradiated Sm-153 (LSA)

The Sm-153 prepared as in Example 1 will be used to prepare doses of Sm-153-DOTMP. These doses will be used to treat patients suffering from bone cancer. Patients are to be repeatedly treated (10 times) with 30 mCi of Sm-153-DOTMP as prepared in this example. The first 5 doses will be given at 3 month intervals and the second five doses given at 6 month intervals. After the decay of Sm-153, a NaI crystal will be used to detect the amount of activity in the patients. Even after 10 doses there should be no detectable amounts of activity from long-lived radionuclidic impurities in the treatment found in the patients.

Although the invention has been described with reference to its preferred embodiments, those of ordinary skill in the art may, upon reading and understanding this disclosure, appreciate changes and modifications which may be made which do not depart from the scope and spirit of the invention as described above or claimed hereafter. Accordingly, this description is to be construed as illustrative only and is for the purpose of teaching those skilled in the art the general manner of carrying out the invention.

What is claimed is:

1. A method for the treatment of a patient having bone pain, one or more calcific tumors, or in need of a bone marrow suppressing procedure, comprising administering to said patient Multiple Doses of a pharmaceutically-acceptable formulation of a chelate composition comprising a Clinically Relevant Dosage of the composition of about 0.5 mCi per kg body weight or about 30 mCi for a 70 kg patient, or about 1.0 mCi per kg body weight or about 70 mCi for a 70 kg patient that is therapeutically effective without a quantifiable accumulation of long-lived isotopes and about 50% reduced myelosuppression in the patient, said composition possessing an extended Expiration Date of Sm-153 used to prepare the composition of greater than or equal to about 5 days based on Eu-154 present in the formulation being less than 0.093 µCi Eu-154/mCi Sm-153 and said chelate comprises LSA Sm-153 and DOTMP or a physiologically-acceptable salt thereof.

2. The method of claim 1 wherein the amount of Sm-153 is about 0.3 to 1.5 mCi/kg or more.

3. The method of claim 2 wherein the amount of Sm-153 is about 0.5 mCi/kg.

4. The method of claim 1 wherein the Expiration Date of the Sm-153 used to prepare the chelate composition is about 10 days or more.

5. The method of claim 1 wherein the Multiple Doses are at least 2 doses for a patient that is administered at 3 month intervals.

6. The method of claim 1 wherein the Multiple Doses are at least 10 doses for a patient administered over 3 month intervals for the first 5 doses, then over 6 month intervals for the next 5 doses.

7. The method of claim 1 wherein the composition contains equal to or greater than 0.093 µCi of Eu-154 per mCi of Sm-153 at expiry.

8. The method of claim 1 wherein the pharmaceutically-acceptable formulation comprises one or more of a suitable solvent, preservatives, diluents, excipients and buffers.

9. The method of claim 8 wherein the formulation solvent is water, aqueous alcohols or glycols.

10. The method of claim 5 wherein the Multiple Doses are at least 5 to 100 doses for a patient.

* * * * *